US011771476B2

United States Patent
Krause et al.

(10) Patent No.: US 11,771,476 B2
(45) Date of Patent: *Oct. 3, 2023

(54) APPARATUS AND METHOD FOR FENESTRATED SCREW AUGMENTATION

(71) Applicant: Stryker European Operations Holdings LLC, Kalamazoo, MI (US)

(72) Inventors: Steven F. Krause, Oakland, NJ (US); Abram Reitblat, Monroe, NY (US)

(73) Assignee: Stryker European Operations Holdings LLC, Kalamazoo, MI (US)

(*) Notice: Subject to any disclaimer, the term of this patent is extended or adjusted under 35 U.S.C. 154(b) by 303 days.

This patent is subject to a terminal disclaimer.

(21) Appl. No.: 16/784,372

(22) Filed: Feb. 7, 2020

(65) Prior Publication Data

US 2020/0170690 A1 Jun. 4, 2020

Related U.S. Application Data

(63) Continuation of application No. 16/038,555, filed on Jul. 18, 2018, now Pat. No. 10,595,912, which is a
(Continued)

(51) Int. Cl.
*A61B 17/70* (2006.01)
*A61B 17/56* (2006.01)

(52) U.S. Cl.
CPC ...... *A61B 17/7074* (2013.01); *A61B 17/7032* (2013.01); *A61B 17/7037* (2013.01);
(Continued)

(58) Field of Classification Search
CPC ............ A61B 17/7074; A61B 17/7032; A61B 17/7082; A61B 17/7086; A61B 17/7035;
(Continued)

(56) References Cited

U.S. PATENT DOCUMENTS

| 4,653,487 A | 3/1987 | Maale |
| 4,653,489 A | 3/1987 | Tronzo |

(Continued)

FOREIGN PATENT DOCUMENTS

WO 2011080426 A2 7/2011

OTHER PUBLICATIONS

Extended European Search Report issued in Appln. No. 22203680.8 dated Dec. 21, 2022 (4 pages).

*Primary Examiner* — Jan Christopher L Merene
(74) *Attorney, Agent, or Firm* — Lerner David LLP

(57) ABSTRACT

A surgical instrument includes a cannulated body extending along an axis and having a first working end spaced along the axis from a second working end. The surgical instrument may be used with a fenestrated screw assembly, a delivery unit, and an alignment guide wire. The first working end of the surgical instrument is configured to transmit a force to a delivery unit in a direction about the axis and the second working end is configured to transmit a force to a delivery unit in a direction generally transverse to the axis. The first working end may be used to rotate the delivery unit to thereby removably attach the delivery unit to the fenestrated screw assembly. The surgical instrument may be repositioned to engage the second working end with the proximal end of the delivery unit to maintain the rotational position of the delivery unit.

18 Claims, 8 Drawing Sheets

Related U.S. Application Data continuation of application No. 15/286,039, filed on Oct. 5, 2016, now Pat. No. 10,052,140.

(52) U.S. Cl.
CPC ...... *A61B 17/7082* (2013.01); *A61B 17/7083* (2013.01); *A61B 17/7085* (2013.01); *A61B 17/7086* (2013.01); *A61B 17/7091* (2013.01); *A61B 2017/564* (2013.01)

(58) Field of Classification Search
CPC ............ A61B 17/8685; A61B 17/8665; A61B 17/8615; A61B 17/7083; A61B 17/7011; A61B 17/7098; A61B 17/7076; A61B 17/7085; A61B 17/8816; A61B 17/8805; A61B 17/864; A61B 17/8824; A61B 2017/564; A61B 2017/0023; A61B 90/94; A61B 2090/037; A61B 2090/061; A61B 17/8802; A61B 17/8833; A61B 17/8086
USPC .............. 606/246–279, 300–315, 92–95, 99; 81/60, 177.2, 57.5, 124.4
See application file for complete search history.

(56) References Cited

U.S. PATENT DOCUMENTS

| | | | |
|---|---|---|---|
| 5,879,948 A * | 3/1999 | Van Pelt | G01N 33/0045 436/81 |
| 6,048,343 A | 4/2000 | Mathis et al. | |
| 6,214,012 B1 | 4/2001 | Karpman et al. | |
| 6,554,830 B1 | 4/2003 | Chappius | |
| 6,565,572 B2 | 5/2003 | Chappius | |
| 6,679,890 B2 | 1/2004 | Margulies et al. | |
| 6,730,095 B2 | 5/2004 | Olson, Jr. et al. | |
| 6,814,734 B2 | 11/2004 | Chappuis et al. | |
| 7,004,945 B2 | 2/2006 | Boyd et al. | |
| 7,338,493 B1 | 3/2008 | Vandewalle | |
| 7,354,442 B2 | 4/2008 | Sasso et al. | |
| 7,473,267 B2 | 1/2009 | Nguyen et al. | |
| 7,608,097 B2 | 10/2009 | Kyle | |
| 7,615,070 B2 | 11/2009 | Biscup | |
| 7,699,852 B2 | 4/2010 | Frankel et al. | |
| 7,717,947 B1 | 5/2010 | Wilberg et al. | |
| 7,824,411 B2 | 11/2010 | Varieur et al. | |
| 7,824,413 B2 | 11/2010 | Varieur et al. | |
| 7,842,044 B2 | 11/2010 | Runco et al. | |
| 7,846,093 B2 | 12/2010 | Gorek et al. | |
| 7,909,830 B2 | 3/2011 | Frigg et al. | |
| 8,007,518 B2 | 8/2011 | Winslow et al. | |
| 8,062,270 B2 | 11/2011 | Sweeney | |
| 8,070,785 B2 | 12/2011 | Biscup | |
| 8,083,775 B2 | 12/2011 | Winslow et al. | |
| 8,097,024 B2 | 1/2012 | Winslow et al. | |
| 8,123,751 B2 | 2/2012 | Shluzas | |
| 8,211,153 B2 | 7/2012 | Shaolian et al. | |
| 8,211,155 B2 | 7/2012 | Winslow et al. | |
| 8,211,156 B2 | 7/2012 | Andersen et al. | |
| 8,216,281 B2 | 7/2012 | Winslow et al. | |
| 8,303,598 B2 | 11/2012 | Frankel et al. | |
| 8,303,602 B2 | 11/2012 | Biedermann et al. | |
| 8,317,838 B2 | 11/2012 | Nguyen et al. | |
| 8,333,792 B2 | 12/2012 | Winslow et al. | |
| 8,337,536 B2 | 12/2012 | Mitchell et al. | |
| 8,343,201 B2 | 1/2013 | Biyani et al. | |
| 8,357,184 B2 | 1/2013 | Woolley et al. | |
| 8,366,717 B1 | 2/2013 | Jordan et al. | |
| 8,372,126 B2 | 2/2013 | Trieu et al. | |
| 8,382,808 B2 | 2/2013 | Wilberg et al. | |
| 8,551,141 B2 | 10/2013 | Gephart et al. | |
| 8,556,947 B2 | 10/2013 | Dorawa et al. | |
| 8,568,420 B2 | 10/2013 | O'Halloran et al. | |
| 8,574,273 B2 | 11/2013 | Russell et al. | |
| 8,579,948 B2 | 11/2013 | Biedermann et al. | |
| 8,584,555 B2 | 11/2013 | Chan | |
| 8,608,802 B2 | 12/2013 | Bagga et al. | |
| 8,641,719 B2 | 2/2014 | Gephart et al. | |
| 8,690,930 B2 | 4/2014 | Biedermann et al. | |
| 8,734,338 B2 | 5/2014 | Gorek et al. | |
| 8,747,411 B2 * | 6/2014 | Mitchell | A61B 17/7098 606/104 |
| 8,801,722 B2 | 8/2014 | Aeschlimann et al. | |
| 8,801,800 B2 | 8/2014 | Bagga et al. | |
| 8,808,296 B2 | 8/2014 | Frigg et al. | |
| 8,821,506 B2 | 9/2014 | Mitchell | |
| 8,870,836 B2 | 10/2014 | Sweeney | |
| 8,900,280 B2 | 12/2014 | Paroth et al. | |
| 8,932,297 B2 | 1/2015 | O'Halloran et al. | |
| 8,945,193 B2 | 2/2015 | Kirschman | |
| 8,974,505 B2 | 3/2015 | Sawa et al. | |
| 8,974,506 B2 | 3/2015 | Wenger et al. | |
| 8,992,587 B2 | 3/2015 | Kirschman | |
| 9,033,988 B2 | 5/2015 | Gephart et al. | |
| 9,050,146 B2 | 6/2015 | Woolley et al. | |
| 9,055,934 B2 | 6/2015 | DiPoto et al. | |
| 9,072,551 B2 | 7/2015 | Paroth et al. | |
| 9,095,395 B2 | 8/2015 | Beger et al. | |
| 9,125,694 B2 | 9/2015 | Butler et al. | |
| 9,131,961 B2 | 9/2015 | Wenger et al. | |
| 9,131,970 B2 | 9/2015 | Kang | |
| 9,149,307 B2 | 10/2015 | Sandstrom et al. | |
| 9,155,563 B2 | 10/2015 | Wenger et al. | |
| 9,155,581 B2 | 10/2015 | Asaad et al. | |
| 9,161,779 B2 | 10/2015 | Gorek et al. | |
| 9,198,692 B1 | 12/2015 | Doose et al. | |
| 9,265,539 B2 | 2/2016 | Biedermann et al. | |
| 9,265,540 B2 | 2/2016 | Kirschman | |
| 9,265,548 B2 | 2/2016 | Jones et al. | |
| 9,271,835 B2 | 3/2016 | Bagga et al. | |
| 9,289,249 B2 | 3/2016 | Ramsay et al. | |
| 9,326,801 B2 | 5/2016 | Poulos | |
| 9,326,804 B2 | 5/2016 | Biedermann et al. | |
| 9,393,062 B2 | 7/2016 | O'Halloran et al. | |
| 9,402,661 B2 | 8/2016 | Reitblat et al. | |
| 10,052,140 B2 * | 8/2018 | Krause | A61B 17/7037 |
| 2005/0021084 A1 | 1/2005 | Lu et al. | |
| 2005/0107800 A1 | 5/2005 | Frankel et al. | |
| 2005/0149036 A1 | 7/2005 | Varieur et al. | |
| 2006/0074445 A1 | 4/2006 | Gerber et al. | |
| 2006/0122614 A1 | 6/2006 | Truckai et al. | |
| 2006/0241600 A1 | 10/2006 | Ensign et al. | |
| 2007/0233123 A1 | 10/2007 | Ahmad et al. | |
| 2007/0239159 A1 | 10/2007 | Altarac et al. | |
| 2007/0299443 A1 | 12/2007 | DiPoto et al. | |
| 2008/0082103 A1 * | 4/2008 | Hutton | A61B 17/7032 606/151 |
| 2009/0157078 A1 | 6/2009 | Mikol | |
| 2009/0264895 A1 | 10/2009 | Gasperut et al. | |
| 2010/0004656 A1 | 1/2010 | Marins Dos Reis, Jr. | |
| 2010/0030224 A1 | 2/2010 | Winslow et al. | |
| 2010/0036437 A1 | 2/2010 | Mitchell et al. | |
| 2010/0114174 A1 | 5/2010 | Jones et al. | |
| 2010/0256688 A1 | 10/2010 | Giersch et al. | |
| 2011/0040337 A1 | 2/2011 | Budassi | |
| 2011/0245881 A1 * | 10/2011 | Mitchell | A61B 17/7098 606/104 |
| 2011/0319946 A1 | 12/2011 | Levy et al. | |
| 2012/0029578 A1 | 2/2012 | Suh | |
| 2012/0046698 A1 | 2/2012 | Kolb et al. | |
| 2012/0123478 A1 | 5/2012 | Winslow et al. | |
| 2012/0143257 A1 | 6/2012 | Winslow et al. | |
| 2012/0143258 A1 | 6/2012 | Winslow et al. | |
| 2012/0143263 A1 | 6/2012 | Darendeliler | |
| 2013/0012999 A1 * | 1/2013 | Petit | A61B 17/7076 606/279 |
| 2013/0238036 A1 | 9/2013 | Sinha | |
| 2013/0345763 A1 | 12/2013 | Kang | |
| 2014/0046379 A1 | 2/2014 | Sweeney | |
| 2014/0074103 A1 | 3/2014 | Mandeen et al. | |
| 2014/0100616 A1 | 4/2014 | Shipp | |
| 2014/0114362 A1 | 4/2014 | Giersch et al. | |
| 2014/0121666 A1 | 5/2014 | Biedermann et al. | |

(56) References Cited

U.S. PATENT DOCUMENTS

| | | | |
|---|---|---|---|
| 2014/0277164 A1* | 9/2014 | Ramsay | A61B 17/7076 606/279 |
| 2014/0316423 A1* | 10/2014 | Schafer | A61B 17/7076 606/104 |
| 2015/0073423 A1 | 3/2015 | Hoefer et al. | |
| 2015/0112392 A1 | 4/2015 | Anand et al. | |
| 2015/0173809 A1 | 6/2015 | Bechtel et al. | |
| 2015/0245856 A1 | 9/2015 | Gephart et al. | |
| 2015/0342658 A1 | 12/2015 | Wenger et al. | |
| 2015/0351808 A1 | 12/2015 | Butler et al. | |
| 2015/0366600 A1 | 12/2015 | Wenger et al. | |
| 2016/0038182 A1 | 2/2016 | Gorek et al. | |
| 2016/0100870 A1 | 4/2016 | Lavigne et al. | |
| 2016/0106472 A1 | 4/2016 | Di Lauro et al. | |
| 2016/0106480 A1* | 4/2016 | Zhou | A61B 17/7086 606/86 A |
| 2016/0220292 A1 | 8/2016 | Biedermann et al. | |
| 2017/0027612 A1* | 2/2017 | Viart | A61B 17/708 |

* cited by examiner

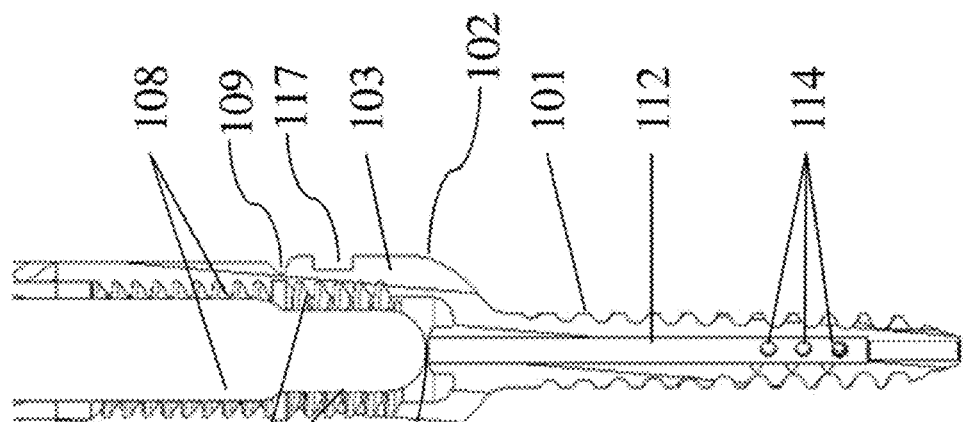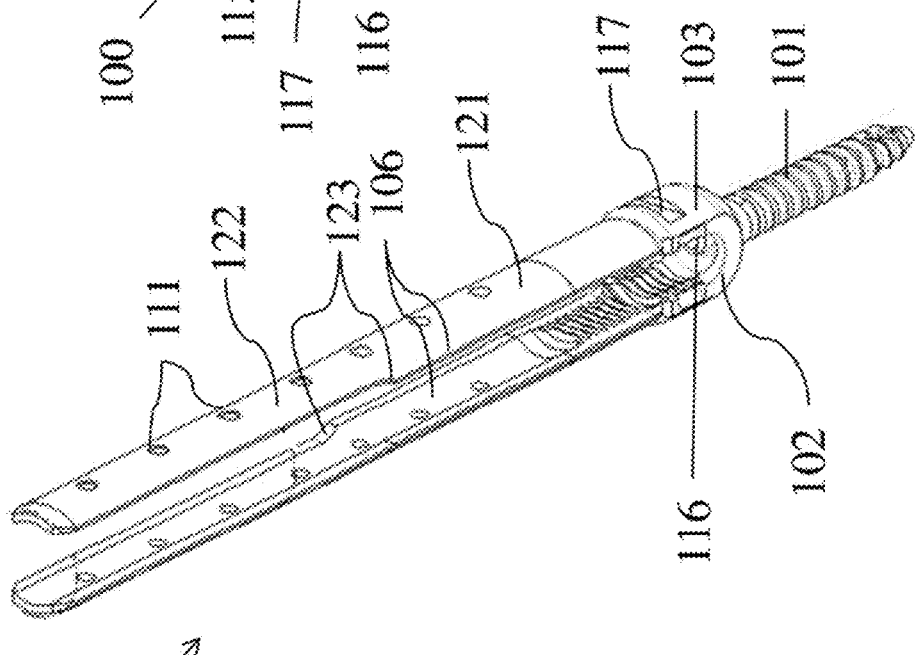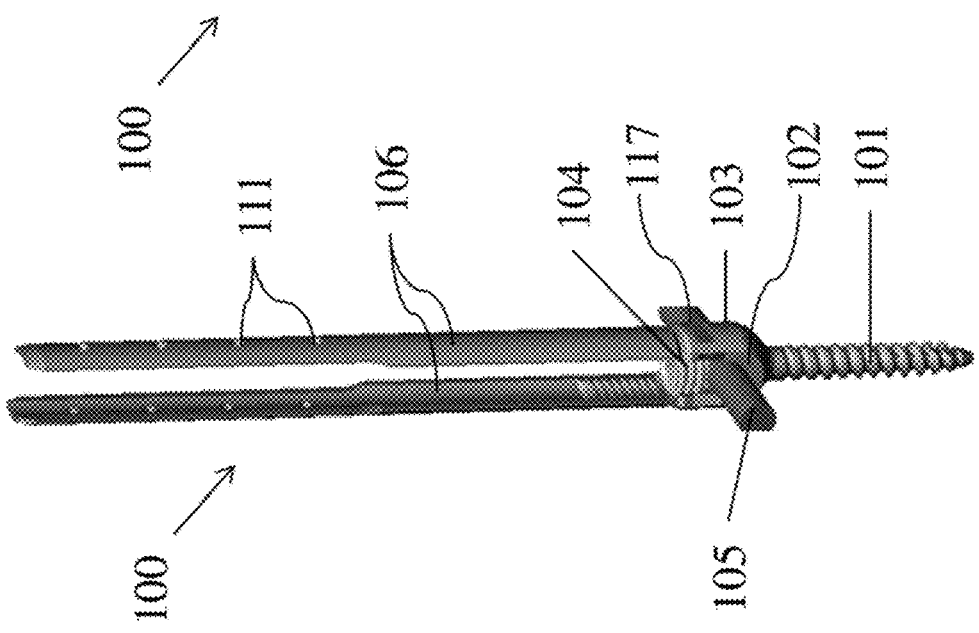

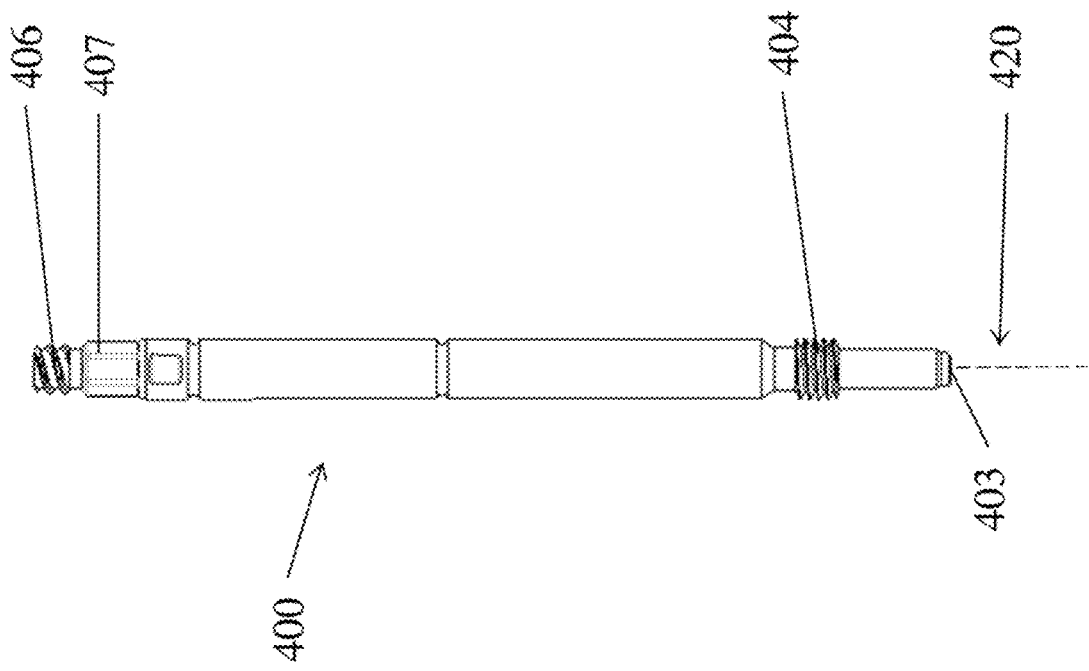
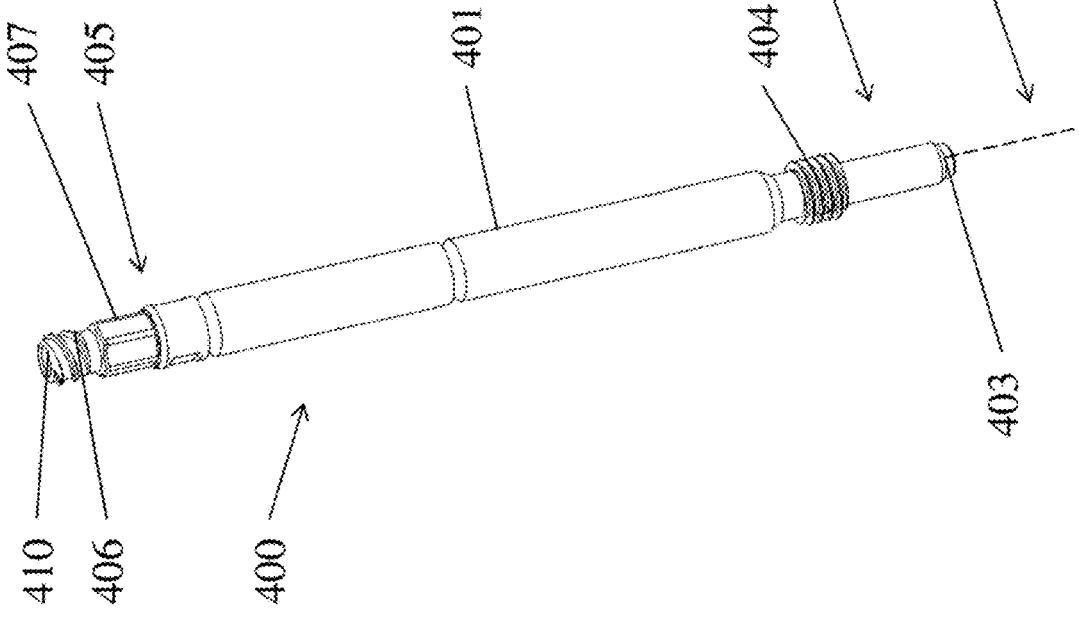

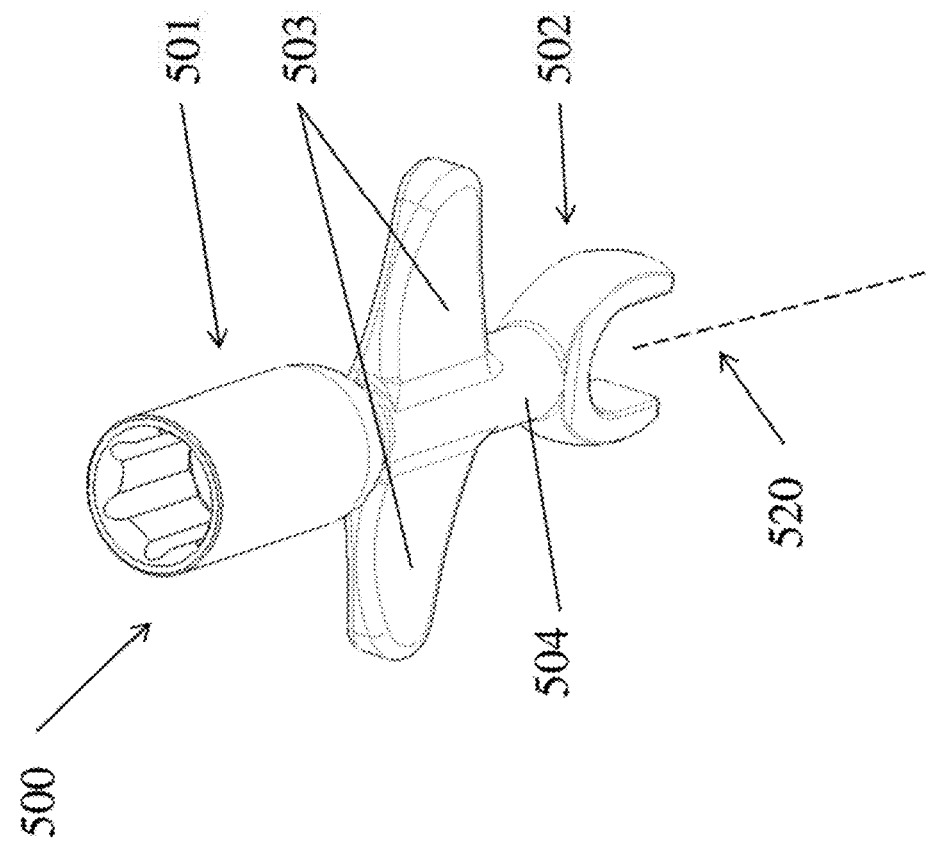
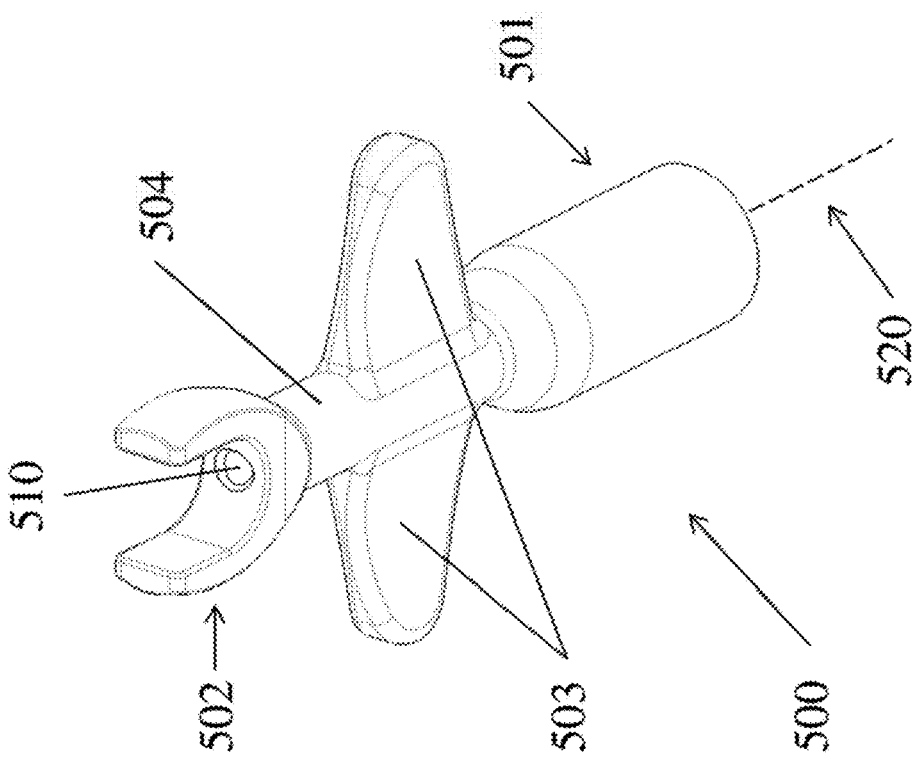

US 11,771,476 B2

1

APPARATUS AND METHOD FOR FENESTRATED SCREW AUGMENTATION

CROSS-REFERENCE TO RELATED APPLICATIONS

This application is a continuation of U.S. application Ser. No. 16/038,555, filed Jul. 18, 2018, which is a continuation of U.S. application Ser. No. 15/286,039, filed on Oct. 5, 2016, now U.S. Pat. No. 10,052,140, the disclosures of which are each incorporated herein by reference.

BACKGROUND OF THE INVENTION

The present invention generally relates to spinal fixation devices, and more particularly to systems and methods for augmentation of fenestrated pedicle screw assemblies.

A technique commonly referred to as spinal fixation is employed for fusing together and/or mechanically immobilizing vertebrae of the spine. Spinal fixation may also be used to alter the alignment of adjacent vertebrae relative to one another so as to change the overall alignment of the spine. Such techniques have been used effectively to treat many degenerative conditions and, in most cases, to relieve pain suffered by the patient.

In some applications, pedicle screws can be inserted into the vertebrae of the spine and connected with a rod in order to provide immobilization and stabilization of the vertebral column Fenestrated pedicle screws are sometimes injected with a cement-like bone augmentation material to aid in anchoring the screw within a vertebral body of reduced bone quality. However, there are some disadvantages associated with current instrumentation and methodologies for augmentation, including solidification of the bone augmentation material in an injecting device prior to injection and leakage of the bone augmentation material during injection into the fenestrated pedicle screw. In some cases, instruments are configured in such a way that they block access to neighboring surgical sites.

There remains room for improvement in the design and use of instrumentation associated with pedicle screw insertion, such as instruments that have enhanced leakage control, preserve space around the surgical site, and streamline and shorten the overall duration of the augmentation procedure.

BRIEF SUMMARY OF THE INVENTION

A first aspect of the present invention is a surgical instrument for use during augmentation of fenestrated pedicle screws. The surgical instrument includes a body extending along an axis and having a first working end spaced from a second working end along the axis, wherein the body is cannulated along the axis from the first working end to the second working end, and wherein the first working end is configured to transmit a force to a surgical device in a direction about the axis and the second working end is configured to transmit a force to a surgical device in a direction generally transverse to the axis.

In accordance with other embodiments of the first aspect, the force that the first working end is configured to transmit may be a rotational force about an axis coincident with or parallel to the axis of the body; and the force that the second working end is configured to transmit may be a rotational force. The first working end may have a first tool construction that is different than a second tool construction of the second working end. The first working end may be a hex drive socket, while the second working end may be an open end wrench.

The body of the surgical instrument may further include a wing between the first and second working ends extending generally transverse to the axis. A second wing may be provided, and it may be symmetrical with the first wing about the axis. The body of the surgical instrument may be comprised of stainless steel and the body may be cannulated, defining a lumen having an internal diameter of about 2.5 mm to accommodate an alignment guide wire.

A second aspect of the present invention is a kit for fenestrated screw augmentation, including a fenestrated screw assembly with a screw body and a tulip, and a surgical instrument including a body extending along an axis and having a first working end spaced from a second working end along the axis, wherein the first working end is configured to transmit a force to a surgical device in a direction about the axis and the second working end is configured to transmit a force to a surgical device in a direction generally transverse to the axis.

In accordance with other embodiments of the second aspect, the body may be cannulated along the axis from the first working end to the second working end. The fenestrated screw assembly in the kit may be a mono-axial pedicle screw assembly or a poly-axial pedicle screw assembly. The fenestrated screw assembly may also include retractor blades extending from the tulip with internal threads. The kit may additionally include a screwdriver. The kit may also include a collar configured to be placed about the retractor blades.

Further, the kit may include a delivery unit having a shaft extending along an axis and a distal end spaced from a proximal end along the axis thereof, wherein the shaft is cannulated along the axis thereof from the distal end to the proximal end. The cannulated shaft of the delivery unit may define a lumen having an internal diameter of about 4.3 mm to accommodate the flow of bone augmentation material therethrough.

The distal end of the delivery unit may include external threads that correspond to the internal threads on the retractor blades. The distal end may also define a mouth that corresponds with an opening of a passage in the screw body. The proximal end of the delivery unit may have external threads and a non-circular interface disposed about the shaft. The non-circular interface may be a hex bit surface. The proximal end of the delivery unit may be dimensioned to engage both the first and second working ends of the surgical instrument for transmission of force from either of the first and second working ends to the delivery unit.

A third aspect of the present invention is a method of fenestrated screw augmentation including removably attaching a distal end of a shaft of a delivery unit to a fenestrated screw assembly, including using a first working end of a body of a surgical instrument in communication with a proximal end of the shaft of the delivery unit to rotate the delivery unit about an axis thereof; and repositioning the surgical instrument to engage a second working end of the surgical instrument with the proximal end of the shaft of the delivery unit.

In accordance with other embodiments of the third aspect, the method may include inserting a screw body of the fenestrated screw assembly into vertebral bone, which may be done with a screwdriver. The method may further include inserting a guide wire through a lumen defined by the body of the surgical instrument, through a lumen defined by the shaft of the delivery unit, and into a passage of a screw body of the fenestrated screw assembly to align the lumen of the delivery unit with the passage of the screw body.

The distal end of the shaft of the delivery unit may be threaded into connection with the fenestrated screw assembly. The distal end of the shaft of the delivery unit may be threaded into connection with retractor blades extending from a tulip of the fenestrated screw assembly. The method may further include placing a collar over a proximal end of the retractor blades. The method may also include placing a rod into a notch of the collar to simulate final rod contouring or placement.

The step of removably attaching the delivery unit may further include transmitting a force from the first working end to the delivery unit in a direction about an axis of the body along which the first and second working ends of the body are spaced. The step of removably attaching may further include applying a force to a wing on the body of the surgical instrument that extends generally transverse to an axis of the body.

The method may further include attaching an injecting device for a bone augmentation material to the delivery unit, which may include using the surgical instrument to maintain the rotational position of the delivery unit. The step of attaching the injecting device may include threading the injecting device to a threaded portion of the proximal end of the delivery unit, and the step of using the surgical instrument to maintain the rotational position of the delivery unit may include engaging the second working end of the surgical instrument with a non-circular interface disposed about the shaft of the delivery unit. The method may further include injecting the bone augmentation material through the lumen of the delivery unit, and into the passage of the screw body, and out of the passage of the screw body through apertures in the screw body.

The method may also involve detaching the injecting device from the delivery unit while using the surgical instrument to maintain the rotational position of the delivery unit. This can be done by engaging the second working end of the surgical instrument with a non-circular interface disposed about the shaft of the delivery unit. The step of detaching may include unthreading the injecting device from a threaded portion of the proximal end of the delivery unit, and the step of using the surgical instrument to maintain the rotational position of the delivery unit may include engaging the second working end of the surgical instrument with a non-circular interface disposed about the shaft of the delivery unit.

The method may further involve manipulating the first or second working end of the surgical instrument coupled with the proximal end of the shaft of the delivery unit to rotatably loosen the distal end of the delivery unit from the fenestrated screw assembly. This step of manipulating may include transmitting a force from the second working end to the delivery unit in a direction generally transverse to an axis of the body along which the first and second working ends of the body are spaced. The method may further involve removing retractor blades attached to a tulip of the fenestrated screw assembly.

A fourth aspect of the present invention is a fenestrated pedicle screw assembly, including a screw body defining a passage along its length and having apertures extending from the passage to an exterior surface of the screw body, a tulip connected with a proximal end of the screw body, two retractor blades each extending from a portion of the tulip at a frangible boundary, and a set screw configured to be threaded into internal threads of the tulip.

In accordance with other embodiments of the fourth aspect, the retractor blades may each include internal threads. The tulip may be mono-axially or poly-axially connected with the proximal end of the screw body. The assembly may further include a spinal rod. The assembly may further include a collar configured to be placed over a proximal end of the retractor blades. The collar may include a notch 120 on its upper surface that is concave to facilitate holding a rod or a rod template. The collar may have extensions that respectively engage with apertures in the retractor blades to maintain the collar in a temporarily fixed position along the length of the retractor blades. The retractor blades may each have a wide distal section that transitions to a narrow proximal section at a taper. The taper may serve as a limiting feature to prevent the collar from being moved distally past the taper. The collar may be an open ring.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 1 is a perspective view of a mono-axial fenestrated pedicle screw assembly with a spinal rod installed.

FIG. 2 is another perspective view of the assembly of FIG. 1.

FIG. 3 is a front sectional view of the assembly of FIG. 1.

FIG. 9 is a perspective view of a delivery unit.

FIG. 10 is a front elevational view of the delivery unit of FIG. 9.

FIGS. 11 and 12 are top and bottom perspective views, respectively, of a hex key.

DETAILED DESCRIPTION

Figure 6:
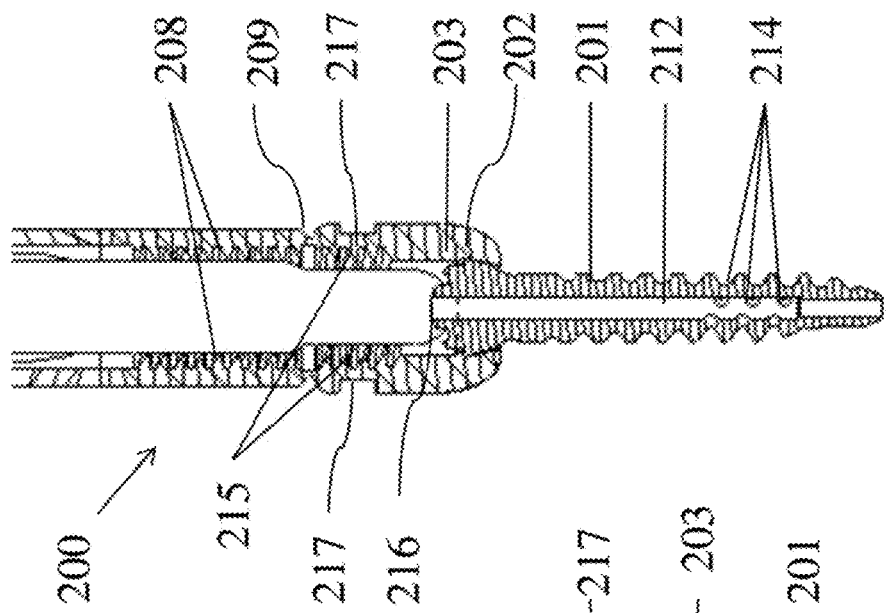
FIG. 6 is a front sectional view of the assembly of FIG. 4.

The present invention relates to systems and methods for augmentation of fenestrated pedicle screws. Those of skill in the art will recognize that the following description is merely illustrative of the principles of the invention, which may be applied in various ways to provide many different alternative embodiments.

Referring to FIGS. 1-3, a mono-axial fenestrated pedicle screw assembly 100 is shown. Assembly 100 includes a screw body 101, a tulip 103, and two retractor blades 106. A spinal rod 105 is installed into tulip 103 and held in place by set screw 104, which is threaded into internal threads 115 of tulip 103. Assembly 100 is a monolithic structure having tulip 103 connected with a proximal end 102 of screw body 101 and retractor blades 106 extending from tulip 103. Tulip 103 includes depressions 117 on both sides for engagement with a surgical tool that may be used later to grasp tulip 103.

Retractor blades 106, each extend from a portion of tulip 103 to facilitate augmentation and rod placement. Retractor blades 106 each extend from a portion of tulip 103 at a frangible or breakable boundary 109. Retractor blades 106 each include internal threads 108 to removably attach to a delivery unit 400, as will be discussed below. External surfaces of blades 106 can include markings to reference the position of a ring or collar 110, described further below.

As shown more clearly in FIG. 3, screw body 101 is cannulated, defining a passage 112, and includes apertures 114 at the distal end of screw body 101 to accommodate the flow of bone augmentation material through passage 112 and out apertures 114 into the surrounding bone structure. The distal end of screw body 101 can include another opening to which passage 112 extends, or may be closed. Three rows of apertures 114 are depicted at the distal end of screw body 101, though more or fewer apertures can be provided at different locations along the length of screw body 101. Passage 112 exits proximal end 102 of screw body 101 at an opening 116 having a raised profiled compared with the adjacent surface of proximal end 102. Opening 116 is configured to be attached with delivery unit 400, as will be discussed below.

Figure 5:
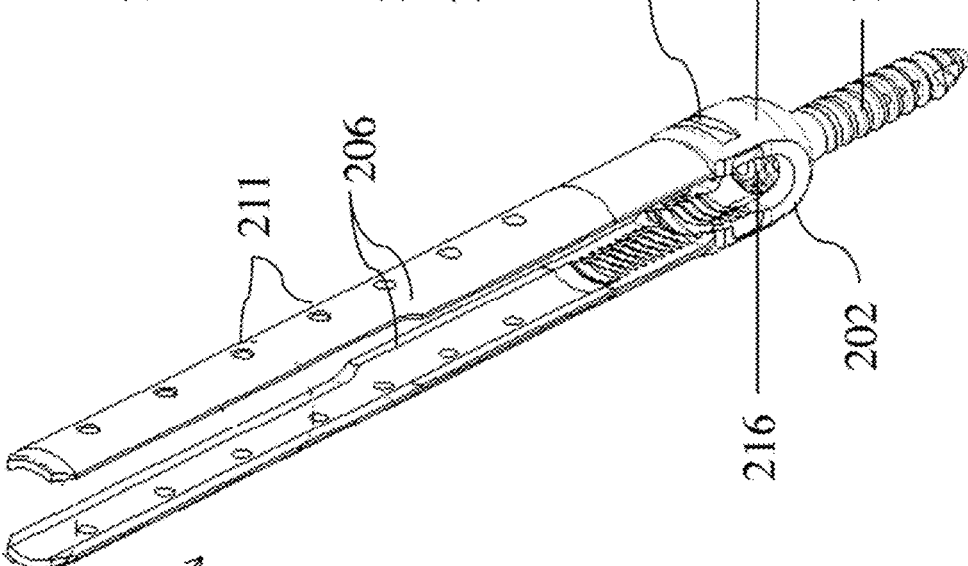
FIG. 5 is another perspective view of the assembly of FIG. 4.
Figure 4:
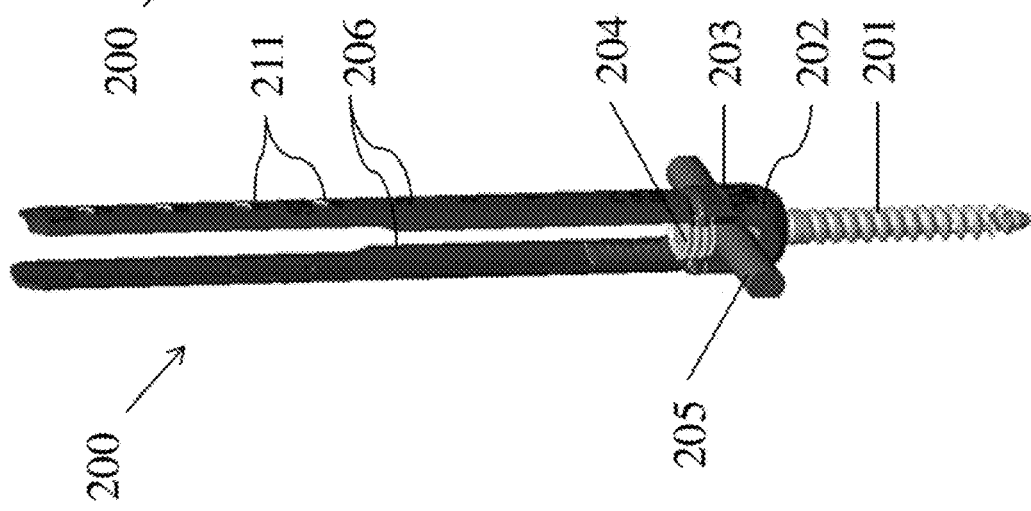
FIG. 4 is a perspective view of a poly-axial fenestrated pedicle screw assembly with a spinal rod installed.

FIGS. 4-6 show a poly-axial fenestrated pedicle screw assembly 200, which has many similar features that are similarly numbered in comparison with assembly 100. Assembly 200 is shown in FIG. 4 with a rod 205 installed and held in place by a set screw 204. Assembly 200 is a two-piece structure having, as one structure, a tulip 203 and two retractor blades 206 each connected with and extending from a portion of tulip 203 at a boundary 209; and, as the other structure, a screw body 201 with proximal end 202.

Tulip 203 can swivel about and form different angles with screw body 201 to facilitate proper rod placement. Tulip includes depressions 217 for external engagement by an instrument. Proximal end 202 of screw body 201 forms an interference fit connection with a distal opening of tulip 203 to create the poly-axial connection. Set screw 204 is threaded into internal threads 215 of tulip 203, while retractor blades 206 each have internal threads 208 for interfacing with delivery unit 400.

As shown in FIG. 6, screw body 201 is also cannulated to define a passage 212 and includes apertures 214. At proximal end 202 of screw body 201, passage 212 exits at opening 216 having a raised profile compared to the adjacent surface of proximal end 202. Opening 216 has a noncircular outer geometry, such as a six lobe hex head, that provides faster and more intuitive engagement with a driver, prevents stripping of the connection, and allows for easy re-engagement of the driver for tightening and loosening adjustments. Opening 216 therefore accommodates an instrument having a similarly configured working end that can be used to rotate screw body 201 during an insertion procedure. The configuration of opening 216 also allows it to be attached with delivery unit 400.

Insertion methods pertaining to mono-axial fenestrated pedicle screw assembly 100 and poly-axial fenestrated pedicle screw assembly 200 are similar in nature. The following description focuses on assembly 100 with additional remarks directed to the differing aspects of the method as it pertains to assembly 200.

Figure 8:
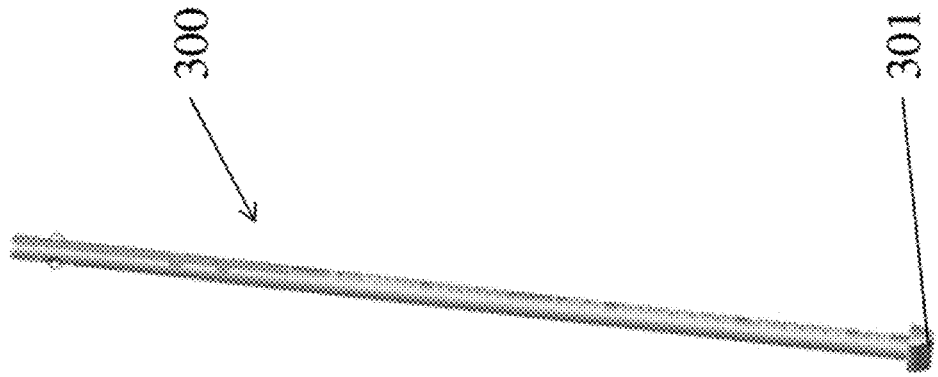
FIG. 8 is a perspective view of an inner drive shaft.

Assembly 100 is first inserted into a vertebral bone using a screw driver, which can include drive shaft 300 as shown in FIG. 8. Drive shaft 300 has a shovel tip 301 dimensioned and configured to interact with tulip 103, which is monolithically connected with screw body 101. Thus, rotational force applied to tulip 103 by shovel tip 301, in turn, drives screw body 101 to install it into the vertebral bone. Drive shaft 300 may be used with a separate driver handle to facilitate rotation of drive shaft 300. Other drive shaft embodiments may have differently shaped tips to engage various configurations of mono-axial fenestrated pedicle screw assembly 100.

Assembly 200 is inserted into the vertebral bone using a screw driver that cooperates with the noncircular outer geometry at the raised profile of opening 216. Such a screw driver can have a six lobe tip to cooperate with a six lobe hex head of opening 216. It is possible for opening 116 of assembly 100 to be configured similarly to opening 216, in which case this same type of screw driver can also be used to insert assembly 100. Once screw body 101 is inserted into the vertebral bone, a delivery unit 400 can be connected to assembly 100. As shown in FIGS. 9 and 10, delivery unit 400 includes a shaft 401 extending along an axis 420. A distal end 402 of shaft 401 is spaced from a proximal end 405 of shaft 401 along axis 420. Delivery unit 400 is cannulated along axis 420 thereof from distal end 402 to proximal end 405, defining a lumen 410 to accommodate the flow of bone augmentation material therethrough. Lumen 410 forms a mouth 403 at distal end 402 that corresponds with openings 116 and 216 of the respective assemblies 100 and 200. Mouth 403 is configured to be seated about openings 116 and 216 to substantially seal the connection between lumen 410 of delivery unit 400 and passage 112, 212 of the respective assembly 100 and 200.

Figure 19:
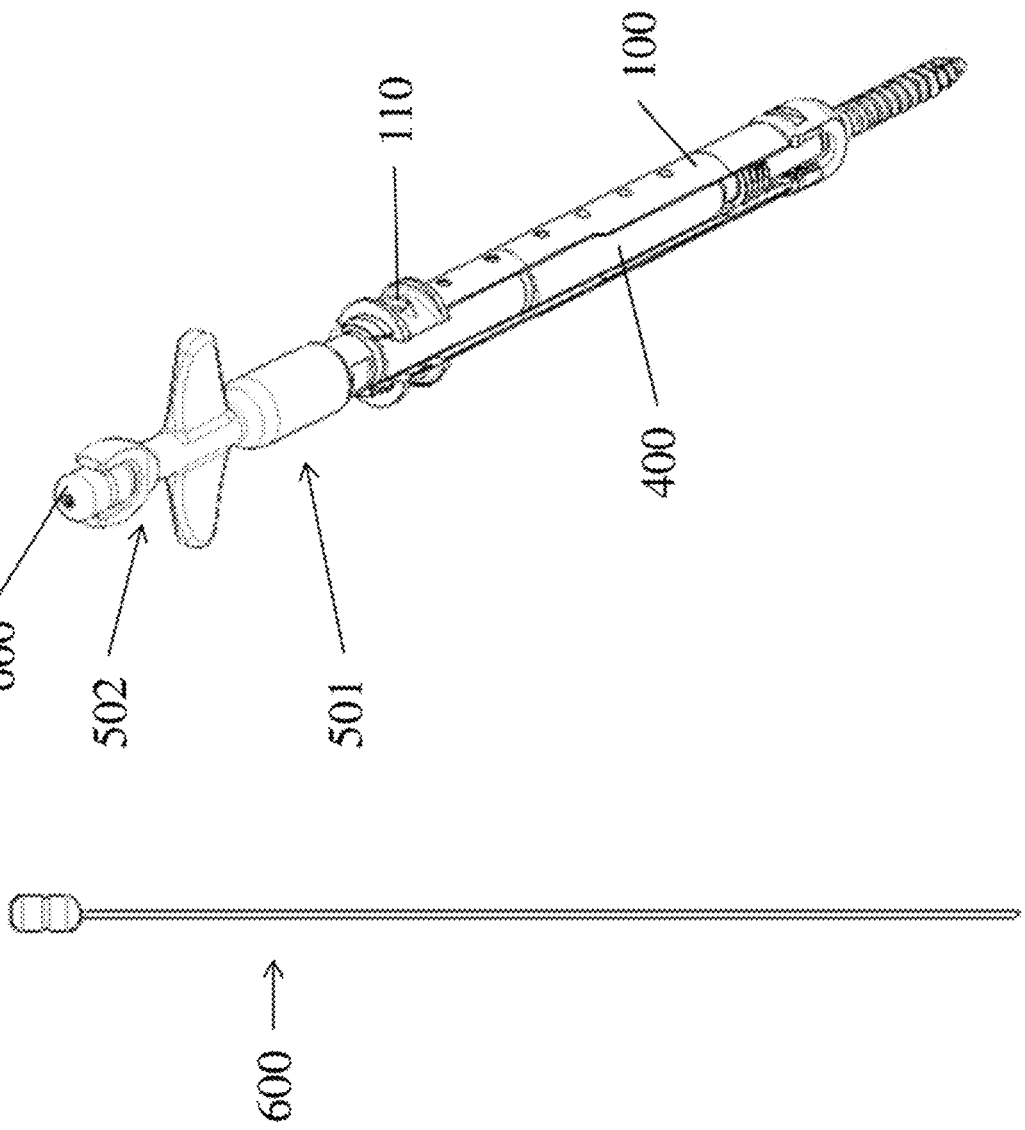

In some embodiments, lumen 410 can have an enlarged diameter 421 of about 4.3 mm along a majority of its length, as shown in FIG. 19. At distal end 402 of shaft 401, lumen 410 may have a reduced diameter 422 of about 1.9 mm, which can correspond with the same diameter in a corresponding screw. This reduced diameter 422 of lumen 401 can be enlarged at the distalmost end to accommodate opening 116 of assembly 100. At proximal end 405 of shaft 401, enlarged diameter 421 of lumen 401 may taper open to an even larger diameter to allow for a taper connection fit with an external instrument. Any of the lengths of lumen 410 can have constant diameters or can be tapered by, for example, 0.2 degrees, 6 degrees, or other similar values.

Distal end 402 of delivery unit 400 has external threads 404 that removably attach to internal threads 108 on retractor blades 106 of assembly 100. This connection maintains an installed position of delivery unit 400 with respect to assembly 100 in order to ensure the connection is secure at the interface between delivery unit 400 and assembly 100 and thereby, prevent leakage during the augmentation procedure. In other embodiments, other attachment means can be used to attach delivery unit 400 to assembly 100, such as a snap-fit attachment feature, a quick release mechanism, a cantilever hook, or the like.

Proximal end 405 of delivery unit 400 includes a portion having external threads 406 to removably attach to an injecting device containing bone augmentation material. Proximal end 405 also includes a non-circular interface 407 disposed about shaft 401, shown here as a hex bit surface. External threads 406 have a maximum outer diameter that is less than a minimum diameter of non-circular interface 407, so that a tool can be utilized to engage non-circular interface 407 without interference from external threads 406. Different embodiments of the delivery unit may use a different attachment means or a different shaped interface on the proximal end. For instance, external threads 406 can instead be provided internally within lumen 410 to accommodate an externally threaded injecting device.

Figure 7:
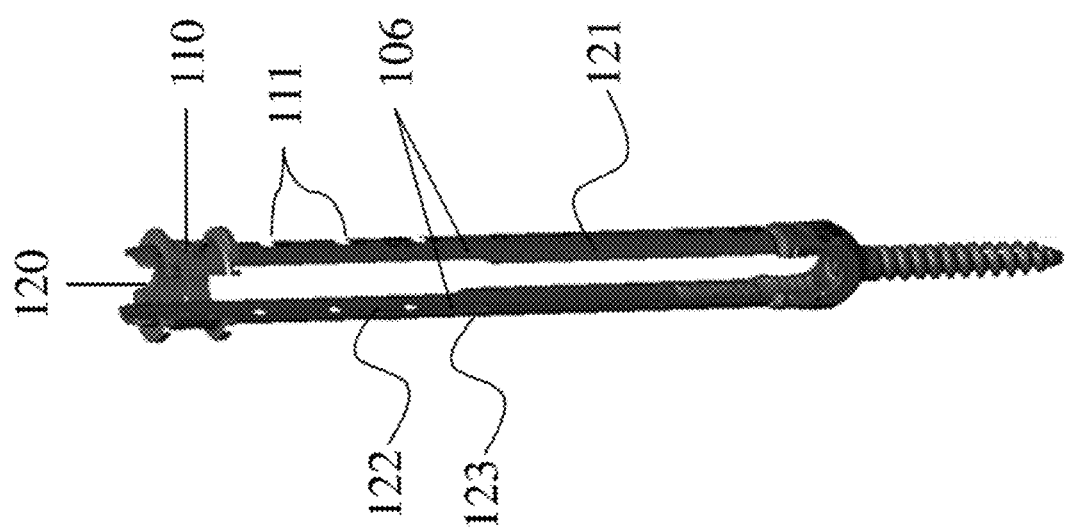
FIG. 7 is a perspective view of an open collar connected with retractor blades of the assembly of FIG. 1.
Figure 14:
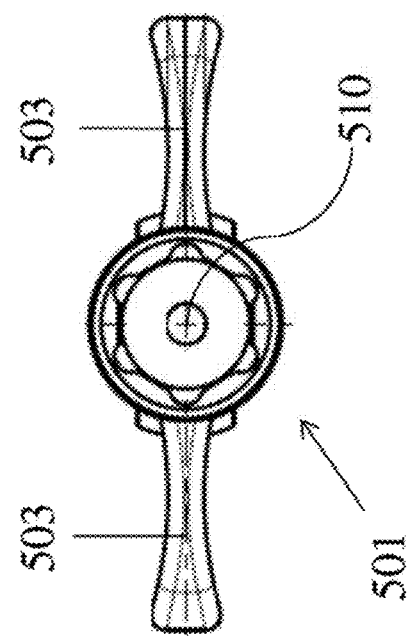
FIG. 14 is a bottom plan view of the hex key of FIG. 11.
Figure 13:
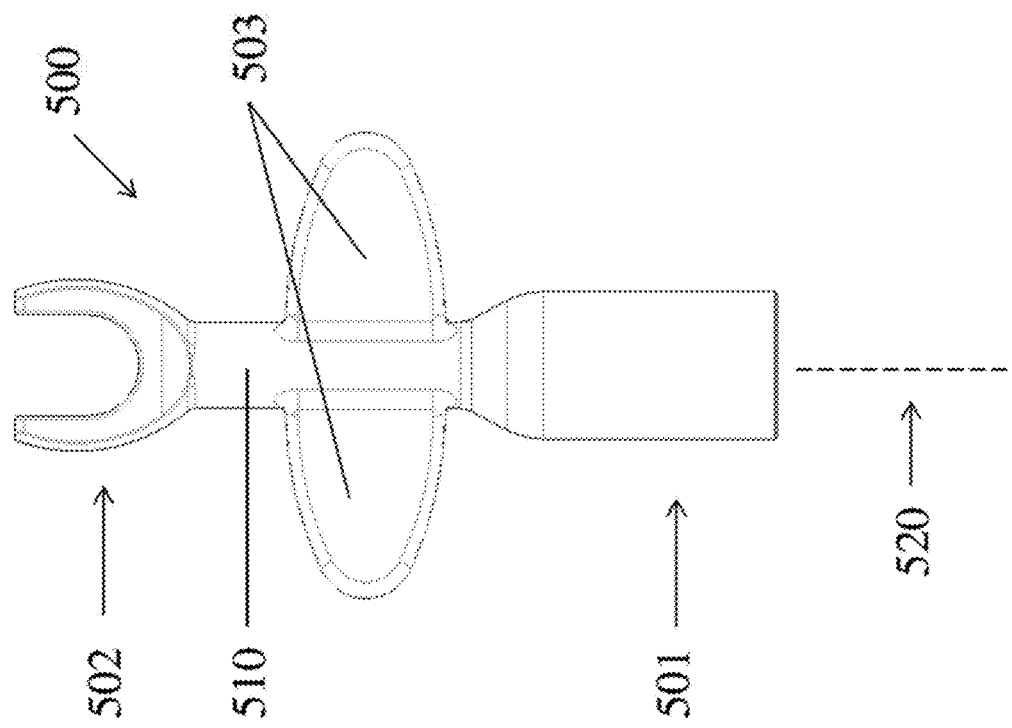
FIG. 13 is a front elevational view of the hex key of FIG. 11.

As shown in FIG. 7, one embodiment of assembly 100 includes an open ring or collar 110 that can be placed over a proximal end of retractor blades 106 and may be utilized to improve the rigidity of blades 106. Collar 110 has an open ended (or unclosed) annular configuration and includes two opposing extensions that respectively engage with apertures 111 in retractor blades 106 to maintain collar 110 in a temporarily fixed position along the length of retractor blades 106. Collar 110 may be placed at multiple positions along the length of blades 106 to accommodate delivery unit 400 and other instruments that operate with assembly 100. Blades 106 each have a wide distal section 121 that transitions to a narrow proximal section 122 at a taper 123. In some embodiments, taper 123 can serve as a limiting feature to prevent collar 110 from being moved distally past taper 123. Collar 110 may be placed either before or after the delivery unit 400 is connected, but is not required to be used in all procedures. Apertures 211 are also shown on retractor blades 206.

The retractor blades 106 may further include markings adjacent the apertures 111 to denote different positions for collar 110 along the length of the retractor blades 106. These markings can be used to indicate the appropriate working length and contour of the spinal rod that will later be installed. That is, positioning multiple collars 110 at the same marking among multiple assemblies 100 allows for rod contouring to mimic the contour of the spine. Each collar 110 includes a notch 120, shown in FIG. 7, on its upper surface. Notch 120 is concave to facilitate holding a rod or a rod template to aid in determining the length and contour of the finally implanted rod. Collar 110 can be placed at the proximal-most marking before using the screwdriver to insert assembly 100. The orientation and placement of collar 110 can thereafter be changed once the screwdriver is removed.

As shown in FIGS. 11 through 14, a hex key 500 is a surgical instrument that can be used to insert, stabilize, and remove delivery unit 400 from assembly 100. Hex key 500 has a cannulated body 504 extending along an axis 520, with a first working end 501 spaced from a second working end 502 along axis 520. The cannulated body 504 defines a lumen 510 extending from first working end 501 to second working end 502 to accommodate an alignment guide wire 600 inserted therein, as discussed further below. In one embodiment, lumen 510 defines an internal diameter of about 2.5 mm for use with alignment guide wire 600 of a similar dimension. Guide wire 600 can have an external diameter of about 1.5 mm Guide wires of smaller diameters may be weak, and in some cases may break during use. Guide wires of larger diameters may be bulkier and unwieldy. The 2.5 mm internal diameter of lumen 510 is configured to cooperate with the 1.5 mm diameter of guide wire 600 to provide ease of use.

First and second working ends 501, 502 have different tool constructions, both of which are dimensioned to engage hex bit surface 407 of delivery unit 400. As shown in FIG. 12, first working end 501 is a hex drive socket. With such a configuration, first working end 501 is configured to transmit a rotational force to delivery unit 400 in a direction about or parallel to axis 520 of hex key 500. That is, hex key 500 can be rotated about axis 520 to rotate delivery unit 400 via non-circular interface 407 on proximal end 405 of delivery unit 400. Hex drive socket 501 can be used to rotatably tighten or loosen delivery unit 400 attached to assembly 100.

Second working end 502 is an open end wrench that is configured to transmit a rotational force to delivery unit 400 in a direction generally transverse to axis 520. That is, second working end 502 can be connected perpendicularly to delivery unit 400 to provide a rotational force about axis 420 of delivery unit 400, which is generally perpendicular to axis 520 when hex key 500 is so oriented. Open end wrench 502 also engages with non-circular interface 407 on proximal end 405 of delivery unit 400 to rotatably tighten or loosen delivery unit 400. Open end wrench 502 can also be used to hold and maintain the rotational position of delivery unit 400 via engagement with non-circular interface 407, while simultaneously allowing access to external threads 406 and lumen 410 of delivery unit 400, particularly when a separate injecting device is connected with proximal end 405 of delivery unit 400 to supply bone augmentation material or another substance.

Hex key 504 also includes two wings 503 extending from body 504 in directions generally transverse to the axis 520. Wings 503 are disposed between the first and second working ends 501, 502 and on opposite sides of body 504 such that they are symmetrical about axis 520. Wings 503 facilitate easier rotation of hex key 504, in particular, to transmit force to delivery unit 400. For example, a physician may grip one or both wings 503 between a thumb and forefinger and apply a force to wing(s) 503 in order to rotate hex key 500. In different embodiments, there may be more or fewer wings on the body of the hex key. More specifically, an embodiment of a hex key can include just one wing.

The method of connecting delivery unit 400 to assembly 100 includes removably attaching distal end 402 of shaft 401 of delivery unit 400 to assembly 400. This includes using first working end 501 of hex key 500 engaged with non-circular interface 407 of proximal end 405 of shaft 401 to attach distal end 402 of delivery unit 400 to assembly 100. Use of hex key 500 in this manner rotates delivery unit 400 about axis 420 so that external threads 404 of delivery unit engage internal threads 108 on retractor blades 106 of assembly 100. Manipulation of hex key 500 can include manipulation of at least one wing 503. Of course, this step could also or alternatively involve using second working end 502.

Figure 17:
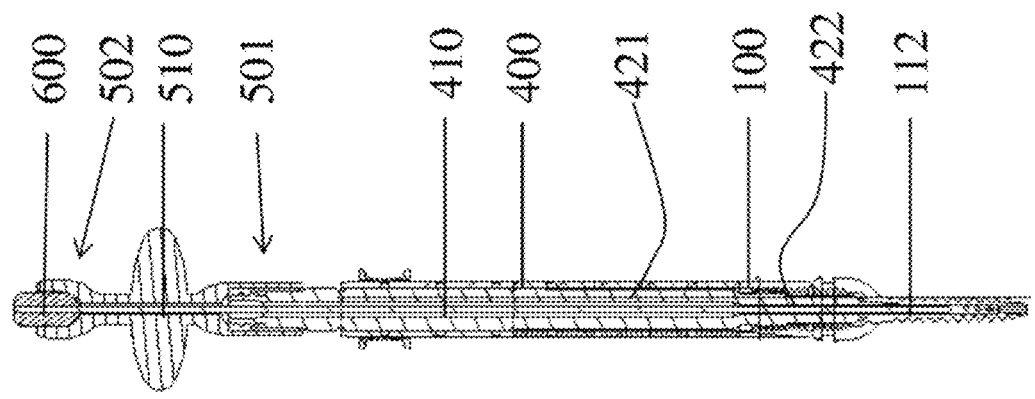
FIG. 17 is a front elevational view of an alignment guide wire.
Figure 18:
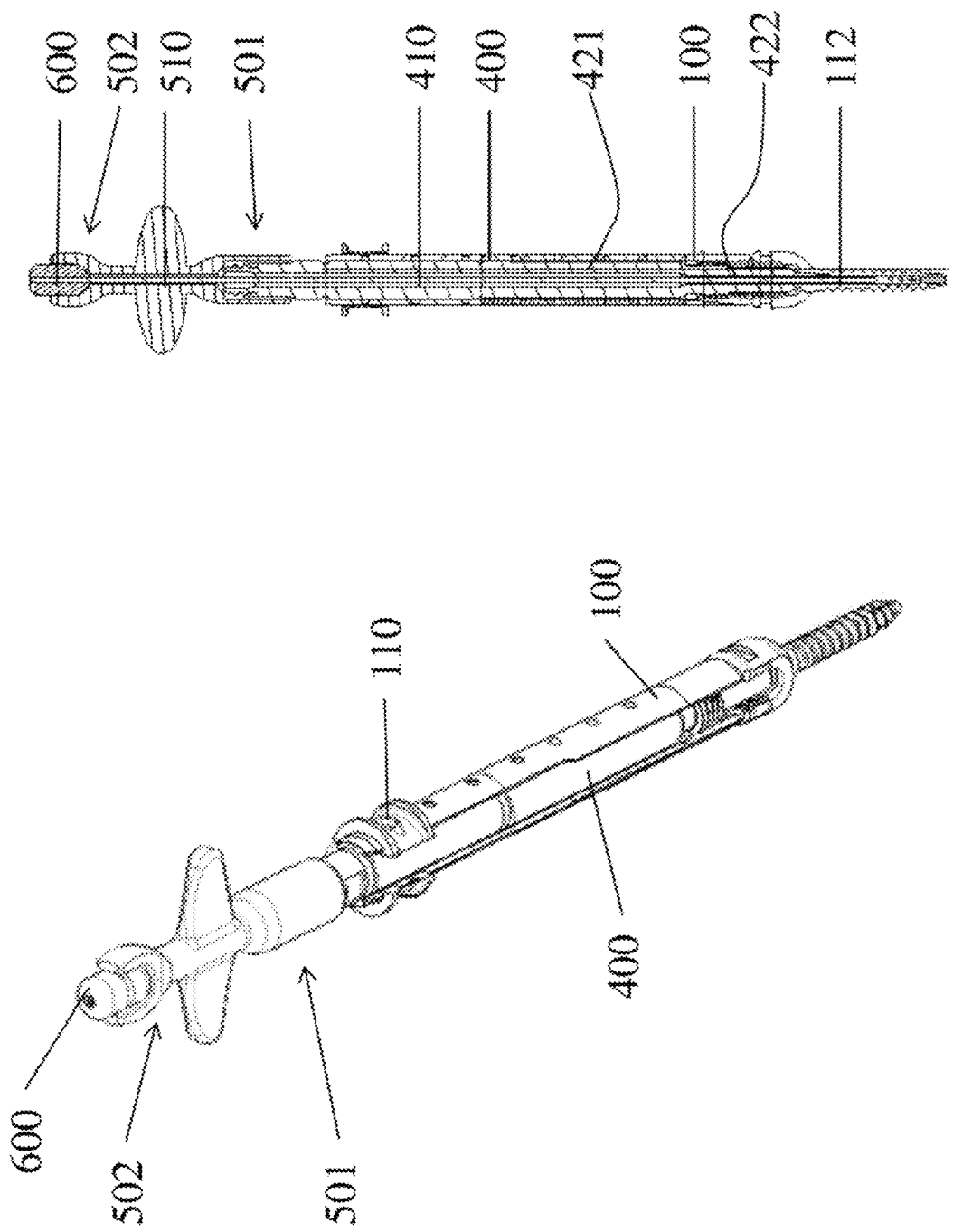
FIGS. 18 and 19 are perspective and front sectional views, respectively, of the delivery unit of FIG. 9, the hex key of FIG. 11, and the alignment guide wire of FIG. 17 assembled with the assembly of FIG. 1.

An alignment guide wire 600, shown in FIG. 17, is used to ensure proper alignment of lumen 410 of delivery unit 400 with passage 112 of screw body 101 of assembly 100. Referring to FIGS. 18 and 19, alignment guide wire 600 is inserted through lumen 510 of the hex key 500, through lumen 410 of delivery unit 400, and into passage 112 of screw body 101. Then, hex key 500 can be used to tighten delivery unit 400 to assembly 100. Thus, this provides a secure connection at the delivery unit-assembly interface to accommodate the flow of the bone augmentation material therethrough.

Once delivery unit 400 is properly seated into assembly 100, alignment guide wire 600 can be removed. First working end 501 of hex key 500 is removed from proximal end 405 of delivery unit 400. An injecting device for a bone augmentation material is attached to delivery unit 400 at external threads 406. During the augmentation procedure, bone augmentation material is injected from the injecting device through lumen 410 of delivery unit 400, into passage 112 of screw body 101, and out of passage 112 through apertures 114 into the surrounding bone structure. The cloud of bone augmentation material should preferably form in the vertebral body closer to the anterior wall thereof. A cloud of approximately 2 cc of bone augmentation material per screw can be used for vertebrae in the lumbar and thoracolumbar areas.

With delivery unit 400 still connected to assembly 100, the bone augmentation material is left to at least partially cure. A bone augmentation material such as CORTOSS sets in approximately 2-4 minutes at body temperature, and in approximately 3.5-8 minutes at room temperature. Removal of delivery unit 400 before at least partial curing can in some cases allow uncured augmentation material to ooze or leak proximally from opening 116 of assembly 100, which is undesirable.

Figure 16:
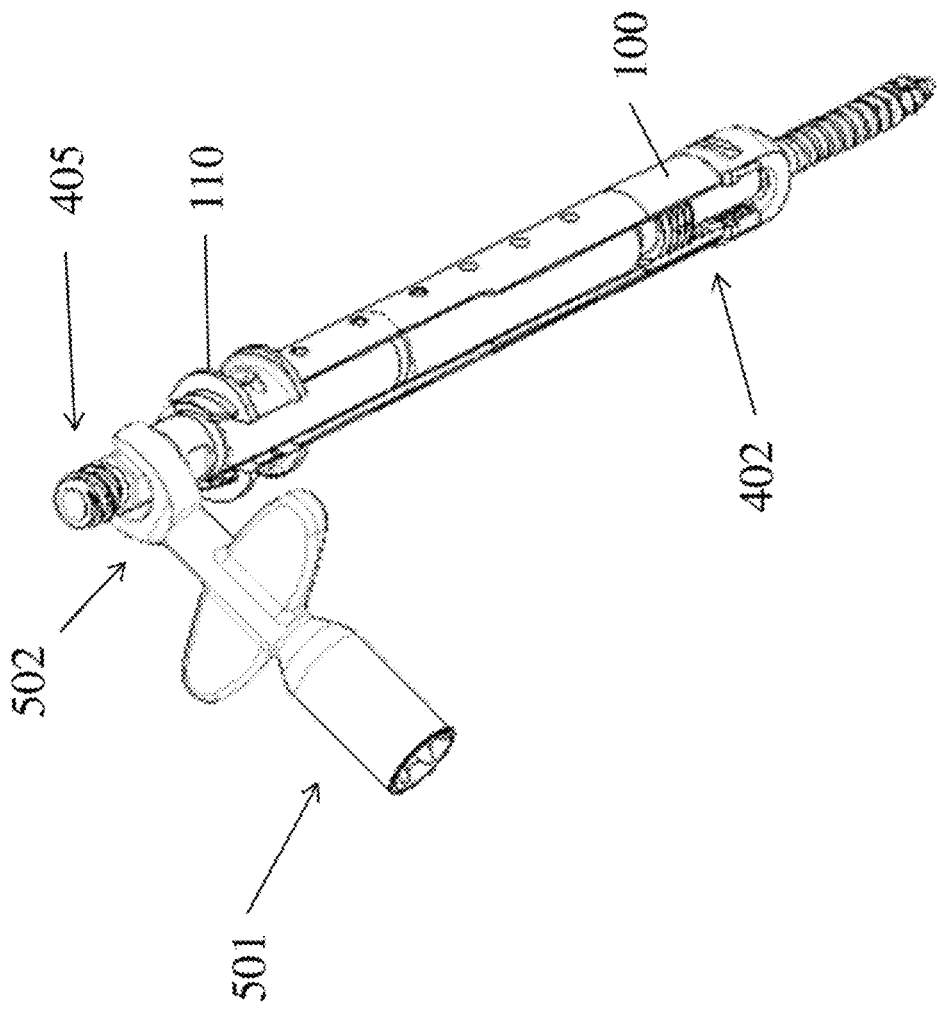
FIG. 16 is a perspective view of the hex key of FIG. 11 assembled with the delivery unit of FIG. 9 and the assembly of FIG. 1.
Figure 15:
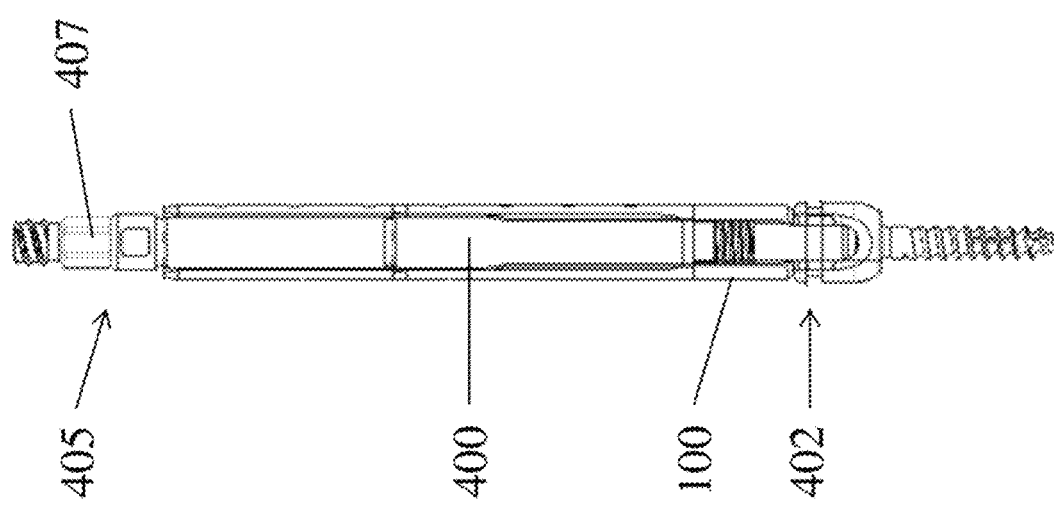
FIG. 15 is a perspective view of the delivery unit of FIG. 9 attached to the assembly of FIG. 1.

As shown in FIG. 16, hex key 500 is repositioned so that second working end 502 is engaged with proximal end 405, and more specifically, with non-circular interface 407. Injecting device can be removed from delivery unit 400, while hex key 500 can be used to maintain the rotational position of delivery unit 400 against the rotational force of the injecting device during its removal. Since delivery unit 400 is secured to assembly 100 and does not rotate, the connection at the delivery unit-screw interface remains secure while the bone augmentation material hardens. Thus, leakage of the bone augmentation material is minimized.

After a sufficient amount of time to allow at least partial curing of the material, which can be about 5 minutes, either first working end 501 or second working end 502 of hex key 500 can be attached to proximal end 405 of delivery unit 400 to loosen distal end 402 of delivery unit 400 from assembly 100. This breaks the at least partially cured material at or near the interface of delivery unit 400 and assembly 100. Any excess augmentation material can be cleared from assembly 100. Spinal rod 105 can then be inserted into tulip 103 and anchored by set screw 104, which is inserted by a driver, such as drive shaft 300. Retractor blades 106 are then removed from tulip 103 by breaking each blade 106 at boundary 109 to separate blades 106 from assembly 100.

Because delivery unit 400 is injected with the bone augmentation material, delivery unit 400 is expected to be used for a single procedure and discarded after one use. Of course, if properly sterilized, delivery unit 400 can be used during multiple procedures so long as its structural integrity is maintained.

Hex key 500, on the other hand, is a separate working instrument from delivery unit 400 and is not used as a conduit for bone augmentation material. One benefit of this construction is that hex key 500 can be sequentially used with multiple delivery units 400 at adjacent surgical sites during a single surgical procedure. Upon proper sterilization, hex key 500 is reusable and need not be discarded after a single use, as is the case with alignment guide wire 600.

Because it is used to insert, secure, and remove delivery unit 400; hex key 500 improves access to the surgical site and avoids interference between delivery units 400 placed at adjacent surgical sites. This is because the construction of delivery unit 400 can be streamlined so that additional features that may otherwise be provided to facilitate its rotation, such as a wing similar to wing 503, need not be included on delivery unit 400. The streamlined delivery units 400 can be located at multiple adjacent surgical sites, which are often in very close proximity, without concern that a particular angulation or rotational orientation of delivery unit 400 will interfere physically with another. By using hex key 500, it is possible to fully attach delivery unit 400 to assembly 100 or assembly 200 in less than approximately thirty seconds. It is also possible to remove the delivery unit from the assembly 100 or assembly 200 in less than approximately one minute.

The removability and reusability of hex key 500 that is separate from each delivery unit 400 contributes to reducing the size of the aggregate delivery units 400 utilized during a procedure, and makes insertion and removal easier by reducing the structural components adjacent the surgical site being attended to at any given moment. Thus, it is much easier and faster to perform the augmentation procedure when the surgical sites are in close proximity, as they often are in these types of procedures. The sequential attachment of delivery units 400 to fenestrated pedicle screw assemblies at adjacent surgical sites will shorten the duration of the augmentation procedure and prevent solidification of the bone augmentation material before injection.

A surgical kit can include assembly 100 and/or assembly 200, and hex key 500. Such a kit may include additional instruments, such as a screw driver, drive shaft 300, delivery unit 400, and/or alignment guide 600. Each of these components can be included in multiple shapes and sizes to accommodate multiple types of procedures.

Hex key 504 is constructed of surgical-grade stainless steel. In other embodiments, hex key 504 may be constructed of other surgical-grade materials that are capable of sterilization and reuse, including titanium, a different metal alloy, ceramic, plastic, and the like. Construction of hex key 504 with two materials is also possible.

Delivery unit 400 is constructed of a translucent material for better viewing and control of the bone augmentation material during the augmentation procedure. In other embodiments, delivery unit 400 may be constructed of stainless steel, titanium, a metal alloy, ceramic, plastic, and the like.

The bone augmentation material can be polymethylmethacrylate (PMMA) or CORTOSS, though other types of bone augmentation materials can be utilized that are surgical grade and allow for desired safety and effectiveness of the augmentation procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of fenestrated screw augmentation comprising:
   disposing a distal end of a shaft of a delivery unit into a fenestrated screw assembly;
   engaging a first working end of a body of a surgical instrument directly with a proximal end of the shaft of the delivery unit;
   inserting a guidewire through a lumen defined by the body of the surgical instrument, through a lumen defined by the shaft of the delivery unit, and into a passage of a screw body of the fenestrated screw assembly to align the lumen of the delivery unit with the passage of the screw body;

securing the delivery unit to the fenestrated screw assembly, including rotating the surgical instrument about a longitudinal axis of the body;

attaching an injecting device to the delivery unit; and repositioning the surgical instrument to engage a second working end of the surgical instrument with the shaft of the delivery unit.

2. The method of claim 1, further comprising injecting a bone augmentation material through the lumen of the delivery unit, into the passage of the screw body and out of the passage of the screw body through apertures in the screw body.

3. The method of claim 1, wherein the step of attaching the injecting device includes threading the injecting device to a threaded portion of the proximal end of the delivery unit.

4. The method of claim 1, wherein the second working end is a wrench.

5. The method of claim 1, wherein the step of repositioning includes engaging the second working end of the surgical instrument with a non-circular interface disposed about the shaft of the delivery unit.

6. The method of claim 1, further comprising detaching the injecting device from the delivery unit.

7. The method of claim 6, wherein the step of detaching further includes unthreading the injecting device from a threaded portion of the proximal end of the delivery unit.

8. The method of claim 7, wherein the second working end of the surgical instrument prevents the delivery unit from rotating while the injection device is unthreaded from the delivery unit.

9. The method of claim 1, wherein the securing the delivery unit to the fenestrated screw assembly includes threading the distal end of the shaft of the delivery unit into connection with the fenestrated screw assembly.

10. The method of claim 9, wherein the step of threading includes threading the distal end of the shaft of the delivery unit into connection with retractor blades extending from a tulip of the fenestrated screw assembly.

11. The method of claim 10, further comprising placing a collar over a proximal end of the retractor blades.

12. The method of claim 11, further comprising placing a rod into a notch of the collar to simulate final rod contouring or placement.

13. The method of claim 12, further comprising manipulating the first working end or a second working end of the surgical instrument to rotatably loosen the distal end of the delivery unit from the fenestrated screw assembly.

14. The method of claim 13, wherein the step of manipulating includes transmitting a force from the second working end of the surgical instrument to the delivery unit in a direction generally transverse to the longitudinal axis of the body of the surgical instrument.

15. The method of claim 13, further comprising removing the retractor blades by separating the retractor blades from a tulip of the fenestrated screw assembly along a frangible boundary.

16. The method of claim 1, wherein the step of securing further includes applying a force to a wing on the body of the surgical instrument that extends generally transverse to the longitudinal axis of the body.

17. The method of claim 1, further comprising inserting a screw body of the fenestrated screw assembly into a vertebral bone with a driver.

18. A method of fenestrated screw augmentation comprising:

disposing a distal end of a shaft of a delivery unit into a fenestrated screw assembly;

engaging a first working end of a body of a surgical instrument directly with a proximal end of the shaft of the delivery unit;

inserting a guidewire through a lumen defined by the body of the surgical instrument, through a lumen defined by the shaft of the delivery unit, and into a passage of a screw body of the fenestrated screw assembly to align the lumen of the delivery unit with the passage of the screw body;

securing the delivery unit to the fenestrated screw assembly, including rotating the surgical instrument about a longitudinal axis of the body;

detaching the delivery unit from the fenestrated screw assembly by manipulating the first working end or a second working end of the surgical instrument;

attaching an injecting device to the delivery unit; and repositioning the surgical instrument to engage a second working end of the surgical instrument with the shaft of the delivery unit.

* * * * *